(12) United States Patent
Hasegawa et al.

(10) Patent No.: US 7,722,818 B2
(45) Date of Patent: May 25, 2010

(54) APPARATUS AND METHOD FOR PREPARING SAMPLES

(75) Inventors: Fuminori Hasegawa, Yamanashi (JP); Tadanori Yoshioka, Tokyo (JP)

(73) Assignees: JEOL Ltd., Tokyo (JP); JEOL Engineering Co., Ltd., Tokyo (JP)

( * ) Notice: Subject to any disclaimer, the term of this patent is extended or adjusted under 35 U.S.C. 154(b) by 1074 days.

(21) Appl. No.: 10/942,752

(22) Filed: Sep. 16, 2004

(65) Prior Publication Data
US 2005/0118065 A1 Jun. 2, 2005

(51) Int. Cl.
*B01L 3/02* (2006.01)
(52) U.S. Cl. ............... 422/100; 250/492.2; 250/492.22; 250/505.1
(58) Field of Classification Search ............... 250/505.1, 250/306, 310, 311, 492.2–492.3; 156/345.39; 422/100
See application file for complete search history.

(56) References Cited

U.S. PATENT DOCUMENTS 5,907,157 A * 5/1999 Yoshioka et al. ......... 250/492.2
6,406,589 B1 * 6/2002 Yanagisawa ............. 156/345.3
6,768,110 B2 * 7/2004 Alani ........................ 250/307
2005/0081997 A1 * 4/2005 Yoshioka et al. ......... 156/345.3

FOREIGN PATENT DOCUMENTS

JP    3263920    8/1997

* cited by examiner

*Primary Examiner*—Michael A Marcheschi
*Assistant Examiner*—Jameson Q Ma
(74) *Attorney, Agent, or Firm*—The Webb Law Firm

(57) ABSTRACT

Apparatus and method capable of preparing samples adapted for observations by electron microscopy. Each sample is ion-etched. During this process, the sample stage is tilted reciprocably left and right about a tilting axis. The sample is ion-etched together with a shielding material. The sample may contain a substance that is not easily etched by the ion beam. In the present invention, such unetched portions are not produced in spite of the presence of the substance. The substance can be separated from the sample. The ion beam is directed at the sample with the boundary defined by an end surface of the shielding material. Portions of the sample at a processing position and its vicinities are etched by the beam.

4 Claims, 11 Drawing Sheets

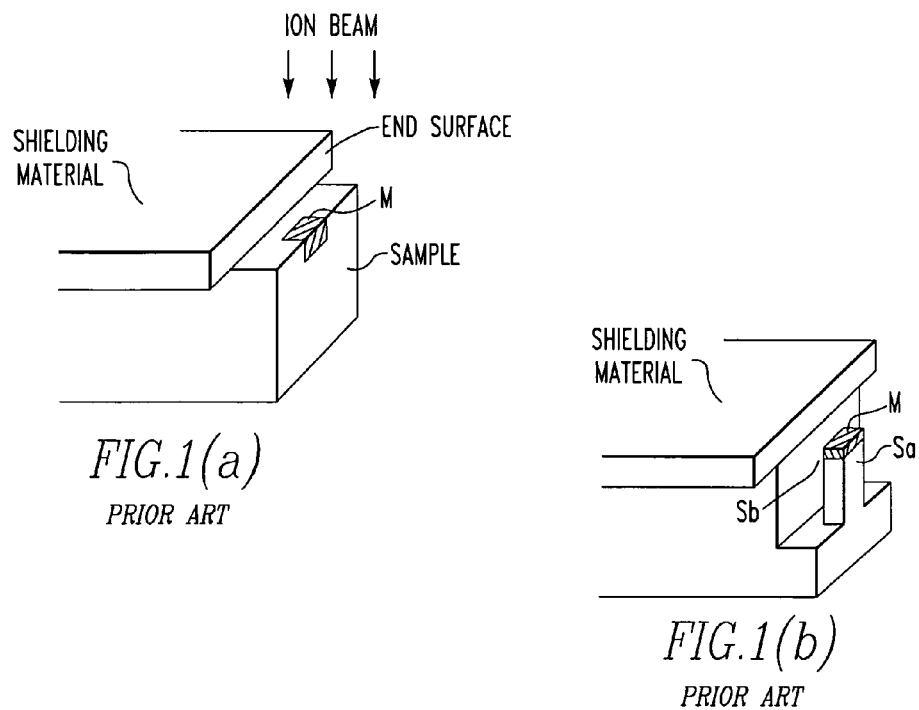
FIG.1(a) PRIOR ART
FIG.1(b) PRIOR ART
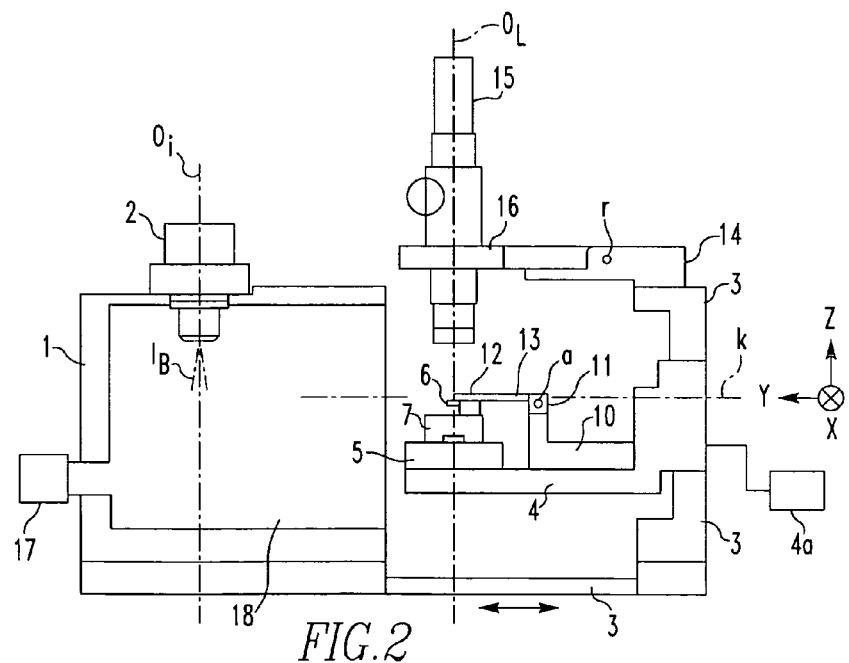
FIG.2

# APPARATUS AND METHOD FOR PREPARING SAMPLES

BACKGROUND OF THE INVENTION

1. Field of the Invention

The present invention relates to an apparatus and method for preparing samples observed on a scanning electron microscope, transmission electron microscope, or other instrument.

2. Description of Related Art

One known apparatus for preparing samples to be observed on a scanning electron microscope (SEM) or transmission electron microscope (TEM) is described, for example, in Japanese Patent No. 3263920. This known apparatus is an ion beam processing system that processes a sample into a shape adapted for SEM or TEM observation by irradiating the sample with an ion beam to etch it.

Furthermore, in the ion beam processing system of Japanese Patent No. 3263920, a shielding material is placed over the sample, and the sample is processed by the ion beam directed at the sample with the boundary defined by an end surface of the shielding material. As a result of this ion beam processing, an electron microscopy sample having a desired cross section is completed.

The sample prepared by the ion beam processing system described above is set on a SEM or TEM. The cross section of the sample produced by the ion etching is irradiated with an electron beam and observed.

If the sample contains a substance M that is not easily etched by the ion beam, as shown in FIG. 1(a), the portion hidden by the substance M is not etched by the ion beam processing system of Japanese Patent No. 3263920, but left behind. As a result, after the etching, the sample assumes a shape, for example, as shown in FIG. 1(b). The unetched portion Sa creates an obstacle in observing the desired cross section Sb by electron microscopy, though the cross section has been produced as a result of considerable effort.

SUMMARY OF THE INVENTION

It is an object of the present invention to provide an apparatus and method capable of preparing good samples adapted for observation.

A sample preparation apparatus that achieves this object in accordance with the teachings of the present invention has: (a) an ion beam irradiation device disposed in a vacuum chamber used to irradiate a sample with an ion beam, (b) a tilting sample stage disposed inside the vacuum chamber and having a tilting axis substantially perpendicular to the ion beam, (c) a sample holder placed on the tilting sample stage and holding the sample, and (d) a shielding material placed over the sample stage and shielding a part of the ion beam directed at the sample. The sample is processed by the ion beam while varying the angle of tilt of the sample stage.

Therefore, according to the present invention, an apparatus and method capable of preparing good samples adapted for observation can be offered.

Other objects and features of the present invention will appear in the course of the description thereof, which follows.

BRIEF DESCRIPTION OF THE DRAWINGS

FIGS. 1(a) and 1(b) illustrate the problem with the prior art technique;

FIG. 2 shows a sample preparation apparatus according to the present invention;

DESCRIPTION OF THE PREFERRED EMBODIMENTS

Figure 3A:
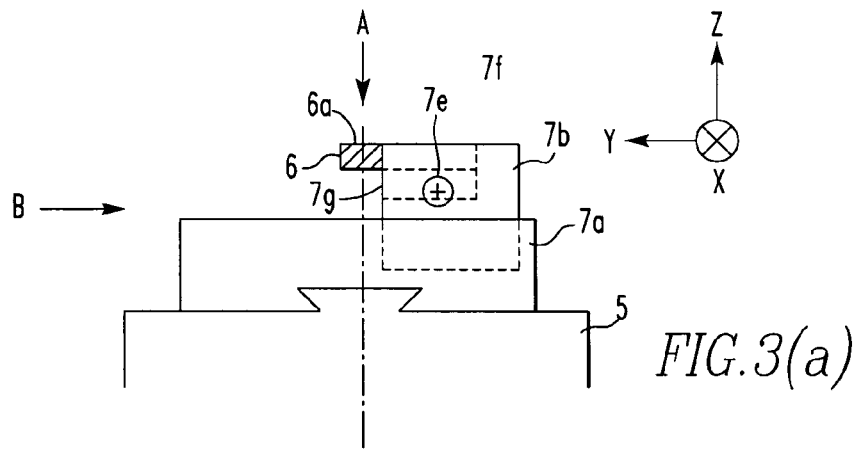
FIGS. 3(a), 3(b), and 3(c) illustrate the sample holder shown in FIG. 2.

Referring to FIG. 2, there is shown a sample preparation apparatus according to the present invention. The structure of this apparatus is first described. The apparatus has a vacuum chamber 1. An ion gun 2 forming an ion beam irradiation means is mounted on the top of the chamber 1. A gas ion gun is used as the ion gun 2. For example, the gas ion gun ionizes Ar gas by electric discharge and releases Ar ions. The center axis $O_i$ of the ion beam $I_B$ emitted from the ion gun 2 is parallel to the Z-axis and perpendicular to the Y-axis.

A sample stage pullout mechanism 3 is mounted to the vacuum chamber 1 such that the mechanism 3 can be opened and closed. In the state of FIG. 2, the pullout mechanism 3 is open. A tilting sample stage 4 is mounted to the pullout mechanism 3 so as to be tiltable about the axis of tilt k that is coincident with the Y-axis. A tilting drive 4a is used to tilt the sample stage 4.

A sample position-adjusting mechanism 5 capable of moving in the X- and Y-directions is disposed on the sample stage 4. The adjusting mechanism 5 can rotate about an axis parallel to the Z-axis.

Figure 3B:
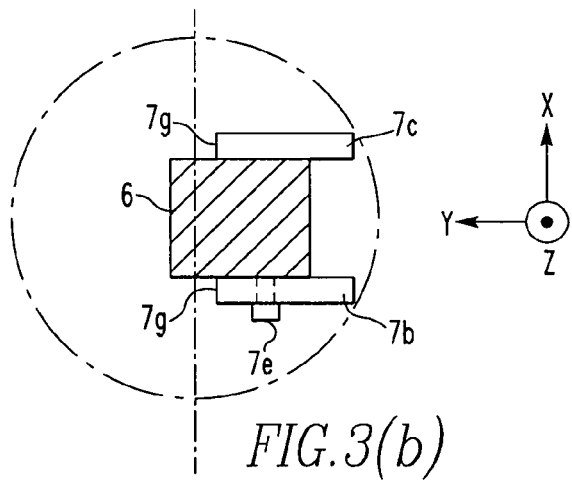
Figure 3C:
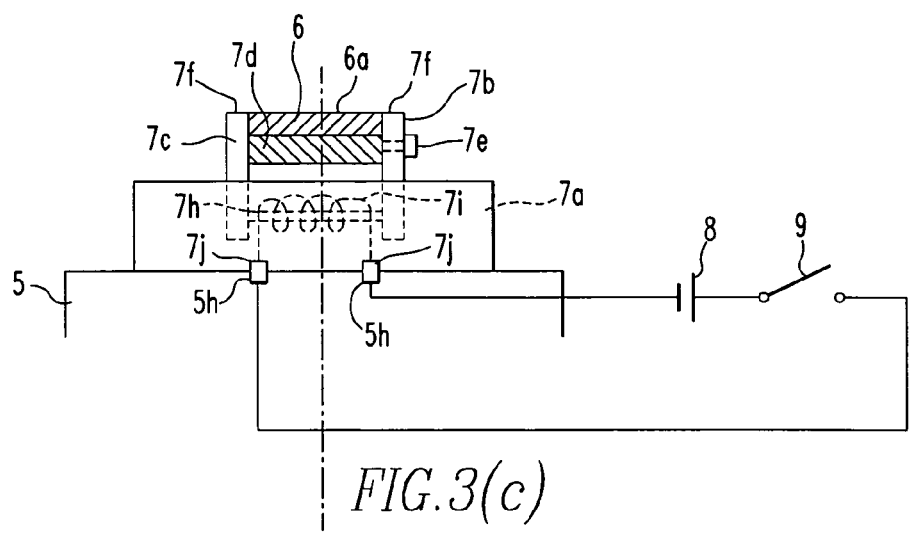

Referring still to FIG. 2, a sample holder 7 holding a sample 6 is mounted to the sample position-adjusting mechanism 5. FIGS. 3(a) to 3(c) illustrate the sample holder 7. FIG. 3(a) is a view taken from a side (X-direction) of the sample holder 7, FIG. 3(b) is a view taken from above the holder 7 (from the direction indicated by the arrow A in FIG. 3(a)), and FIG. 3(c) is a view taken from the front of the holder 7 (from the direction indicated by the arrow B in FIG. 3(a)).

Referring to FIGS. 3(a) to 3(c), a holder-mounting portion 7a is mounted to the X-drive mechanism of the sample position-adjusting mechanism 5. Two yoke pieces 7b and 7c, each in the form of a flat plate, are located opposite to each other and fixedly mounted to the holder-mounting portion 7a. The sample 6 is placed on a placement stage 7d sandwiched between the yoke pieces 7b and 7c. A screw 7e is pressed against the placement stage 7d so that the stage is made stationary. When the placement stage is fixed, the height of the placement stage 7d is adjusted such that the height of the top surface 6a of the sample 6 is coincident with the height of the top surfaces 7f of the yoke pieces 7b and 7c. The sample 6 is placed on the placement stage 7d in such a way that a part of the sample 6 protrudes forward (in the Y-direction) from the front surface 7g of the yoke as shown in FIGS. 3(a) and 3(b).

An electromagnet is incorporated in the sample holder 7 and has a core 7h mounted between the yoke pieces 7b and 7c as shown in FIG. 3(c). The core 7h is located inside the holder-mounting portion 7a. A coil 7i is wound around the core 7h and has an end portion fixed to an electrical contact 7j that is mounted on the bottom surface of the holder-mounting portion 7a.

Another electrical contact 5h is mounted on the top surface of the sample position-adjusting mechanism 5. When the sample holder 7 is mounted to this adjusting mechanism 5, the contact 5h is brought into contact with the contact 7j. The contact 5h is connected with a power supply 8. When an operator switches on a switch 9, the coil 7i is electrically energized to produce a strong magnetic field between the yoke pieces 7b and 7c. Thus, the yoke pieces 7b and 7c function as magnets. The structure of the sample holder 7 of FIG. 2 has been described so far in connection with FIGS. 3(a) to 3(c).

Referring to FIG. 2, a shielding means position-adjusting mechanism 10 is placed on the sample stage 4 and can move in the Y-direction. A shielding material-tilting mechanism 11 is disposed above the shielding means position-adjusting mechanism 10. A shielding material-holding mechanism 13 holding a shielding material 12 is tiltably mounted to the shielding material-tilting mechanism 11 so as to be tiltable about an axis q parallel to the X-axis as indicated by the dotted line in FIG. 4(a).

Figure 4A:
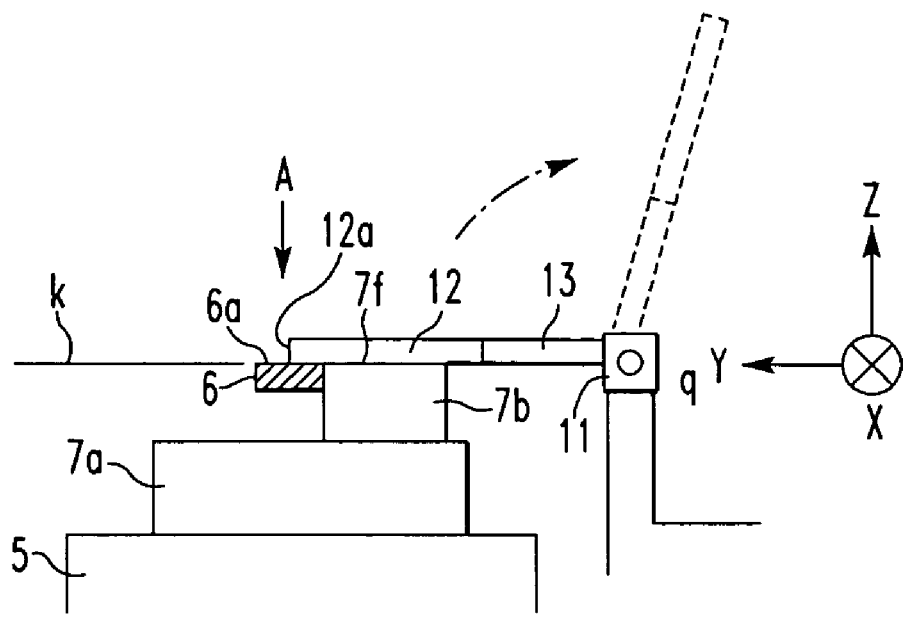
FIGS. 4(a) and 4(b) illustrate the shielding material shown in FIG. 2.
Figure 4B:
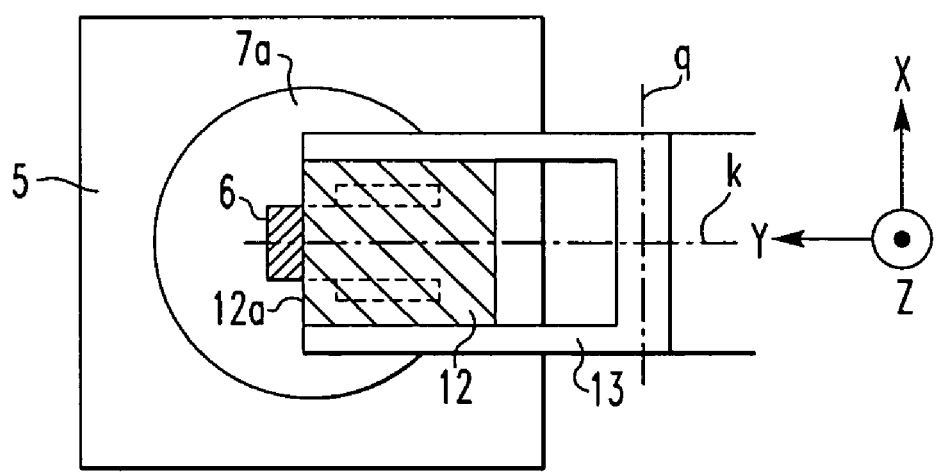

FIG. 4(b) is a view taken from above (in the direction indicated by the arrow A in FIG. 4(a). The shielding material 12 is placed over the sample 6. The shielding material 12 is in the state indicated by the solid line in FIG. 4(a). The shielding material 12 has a flat end surface 12a parallel to the XZ-plane. That is, the end surface 12a is parallel to a plane that is perpendicular to the tilting axis k of the sample stage 4. The front end of the sample 6 is located ahead of the end surface 12a of the shielding material 12 as viewed in the Y-direction. When the shielding material 12 is positioned on the sample 6 as indicated by the solid line as shown in FIG. 4(a), the bottom surface of the shielding material 12 is in intimate contact with the top surface 6a of the sample 6 and with the top surfaces 7f of the yoke pieces 7b and 7c. These surfaces are located on the Y-axis.

The shielding material 12 consists of a magnetic material and an amorphous metal fixedly mounted to the surface of the magnetic material except for portions contacted with the top surfaces 7f of the yoke pieces 7b and 7c. For example, the amorphous material is fixedly mounted to the surface of the magnetic material, for example, by nickel-phosphorus (more than 10% phosphorus) electroless plating.

Figure 5A:
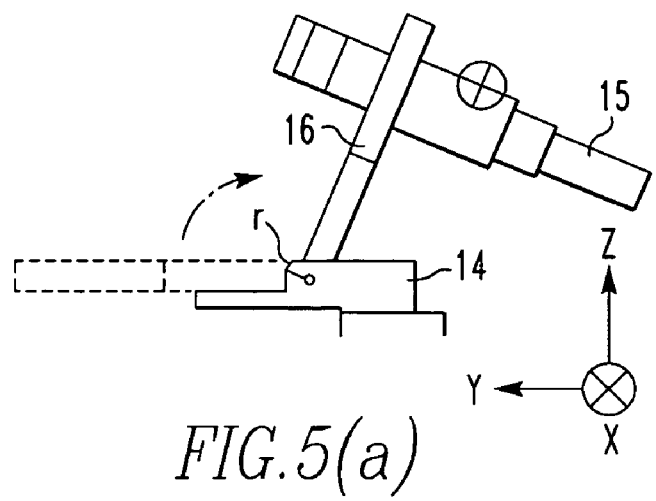
FIGS. 5(a) and 5(b) illustrate the tilt of the optical microscope shown in FIG. 2.

Referring back to FIG. 2, an optical microscope-tilting mechanism 14 is mounted to the top end of the sample stage pullout mechanism 3. An optical microscope position-adjusting mechanism 16 holding an optical microscope 15 is mounted to the tilting mechanism 14 so as to be tiltable about an axis r parallel to the X-axis as shown in FIG. 5(a).

As shown in FIG. 2, the optical microscope-tilting mechanism 14 is so designed that when the optical microscope 15 is placed over the sample 6, the optical axis $O_L$ of the optical microscope 15 is perpendicular to the top surface 6a of the sample 6. That is, the optical axis $O_L$ of the optical microscope 15 is parallel to the Z-axis and substantially parallel to the center axis $O_i$ of the ion beam $I_B$. In the state shown in FIG. 2, the optical microscope position-adjusting mechanism 16 can move the optical microscope 15 in the X- and Y-directions. When an operator manipulates an optical microscope XY-translation knob (not shown) mounted on the adjusting mechanism 16, the optical microscope 15 moves in the X- and Y-directions.

Figure 5B:
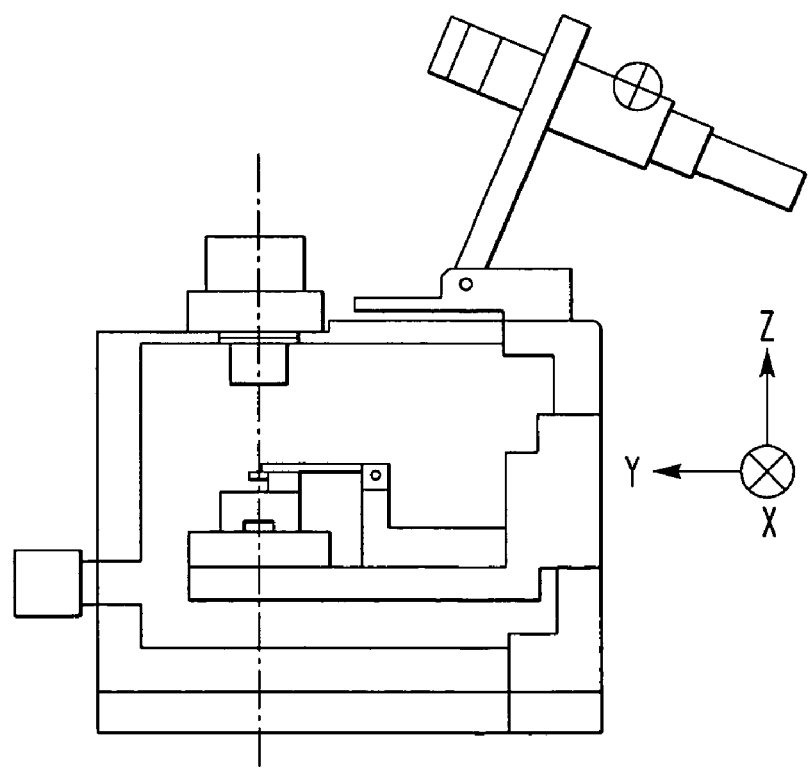

Referring again to FIG. 2, a pumping system 17 evacuates the inside of the vacuum chamber 1, i.e., a processing chamber 18. When the processing chamber 18 is evacuated by the pumping system 17, the optical microscope 15 is retracted from the position located above the sample 6, and the sample stage pullout mechanism 3 is closed as shown in FIG. 5(b). In the sample preparation apparatus shown in FIG. 2, when the sample stage pullout mechanism 3 is closed in this way, the optical microscope 15 is located outside the vacuum chamber 1. The structure of the sample preparation apparatus of FIG. 2 has been described so far.

Positional adjustment of the optical microscope 15, positional adjustment of the shielding material 12, and positional adjustment of the sample 6 are performed prior to ion beam processing of the sample 6.

First, the positional adjustment of the optical microscope 15 is described. To make a mark of the ion beam on the sample 6 for the positional adjustment of the optical microscope, the optical microscope 15 is retracted from the position located above the sample 6 as shown in FIG. 5(b). The sample stage pullout mechanism 3 is closed after the shielding material-holding mechanism 13 has been pulled up as indicated by the dotted line in FIG. 4(a). It is assumed that at this time, the shielding material 12 is not yet mounted to the shielding material-holding mechanism 13. It is also assumed that when the sample stage pullout mechanism 3 is closed, the sample 6 lies on the center axis $O_i$ of the ion beam $I_B$.

After the processing chamber 18 has been pumped down by the pumping system 17, the ion beam $I_B$ is emitted from the ion gun 2 and directed at an arbitrary position on the sample 6 and kept there for a given time. As a result, the sample is etched to make a mark of the ion beam on the sample 6. Then, the sample stage pullout mechanism 3 is pulled out of the vacuum chamber 1 as shown in FIG. 2. The optical microscope 15 is placed on the sample 6. When the optical microscope 15 is set at the sample observational position in this way, the operator observes the mark of the ion beam formed on the sample 6 with the optical microscope 15.

Figure 6A:
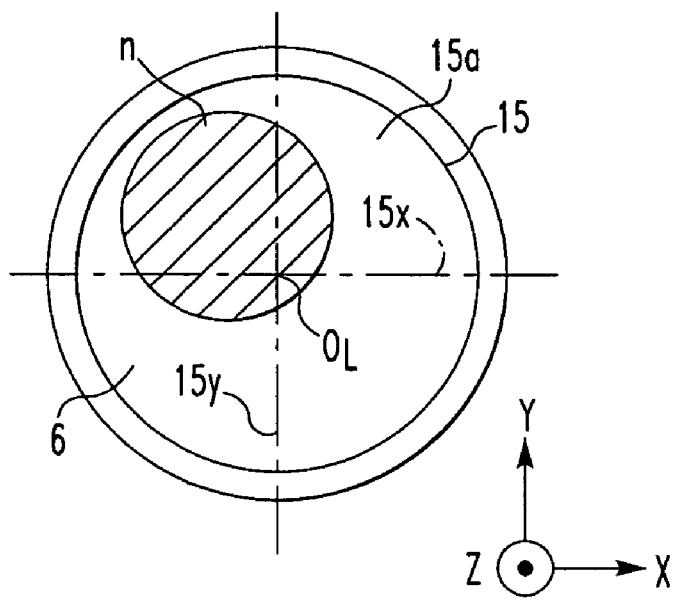
FIGS. 6(a) and 6(b) illustrate the positional adjustment of the optical microscope.

An image of the sample observed through the ocular (eyepiece) 15a of the optical microscope 15 at this time is shown in FIG. 6(a). The mark of the ion beam is indicated by n. The ocular 15a is marked with an X-line 15x parallel to the X-axis and a Y-line 15y parallel to the Y-axis. The intersection of the lines is coincident with the optical axis $O_L$ of the microscope 15.

Figure 6B:
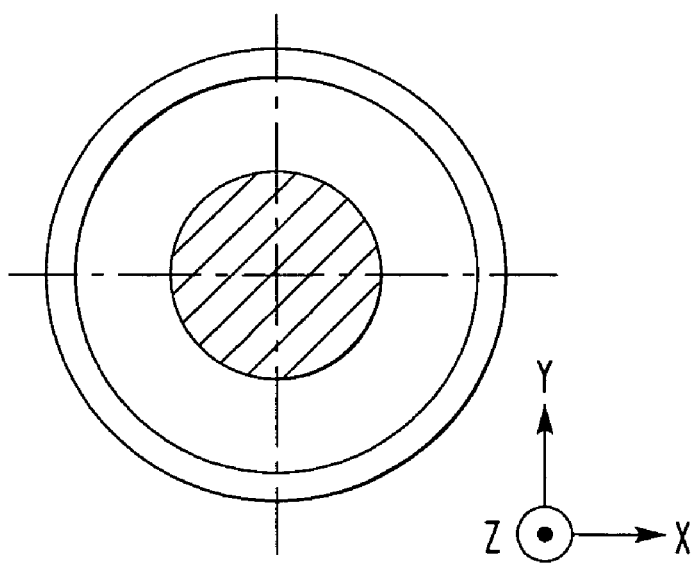

As can be seen from FIG. 6(a), the optical axis $O_L$ of the optical microscope 15 is not coincident with the center of the mark n of the ion beam under this condition. Accordingly, the operator manipulates the optical microscope XY-translation knob of the optical microscope position-adjusting mechanism 16 to bring the optical axis $O_L$ of the optical microscope 15 into coincidence with the center of the mark n of the ion beam as shown in FIG. 6(b).

The positional adjustment of the optical microscope 15 has been described so far. During observation of the sample using the optical microscope 15, the sample processing position placed in position on the optical axis $O_L$ of the ion beam $I_B$ is placed on the center axis $O_i$ by this positional adjustment if the sample stage pullout mechanism 3 is closed. Whenever the position of the center axis $O_i$ of the ion beam $I_B$ varies (e.g., when the ion gun 2 is replaced or cleaned by heating), the positional adjustment of the optical microscope 15 is made.

If the positional adjustment of the optical microscope 15 is performed in this way, positional adjustment of the shielding material 12 is next made under the condition where the sample stage pullout mechanism 3 has been opened as shown in FIG. 2.

First, the shielding material 12 is mounted to the shielding material-holding mechanism 13 as shown in FIG. 4. At this time, the shielding material 12 is mounted to the holding mechanism 13 such that the end surface 12a of the shielding material 12 becomes parallel to the X-axis as shown in FIG. 4(b), i.e., such that the end surface 12a of the shielding material 12 becomes vertical to the tiling axis k of the sample stage. Furthermore, the optical microscope 15 is placed over the sample 6 as shown in FIG. 2.

Figure 7A:
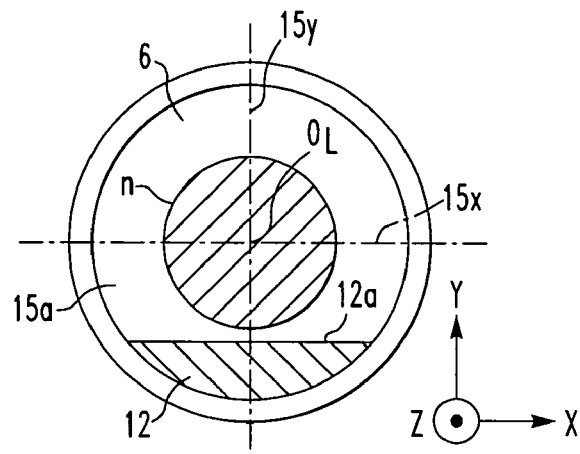
FIGS. 7(a) and 7(b) illustrate the positional adjustment of a shielding material.
Figure 7B:
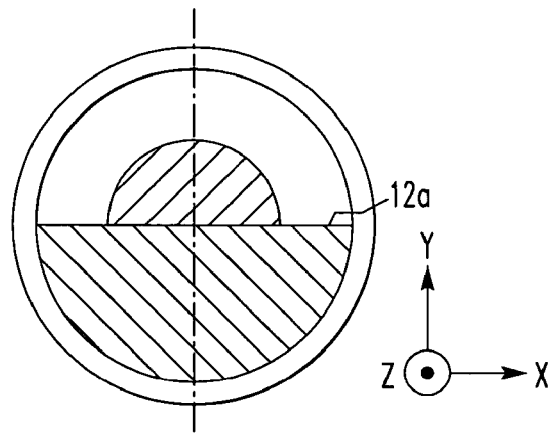

The operator observes the shielding material 12 placed over the sample 6 with the optical microscope 15. The image observed through the ocular 15a of the optical microscope 15 at this time is shown in FIG. 7(a). The end surface 12a of the shielding material 12 is observed together with the mark n of the ion beam. As can be seen from FIG. 7(a), the end surface 12a of the shielding material parallel to the X-axis is not located on the optical axis $O_L$ of the microscope 15 under this condition. Accordingly, the operator manipulates the shielding means Y-translation knob of the shielding means position-adjusting mechanism 10 while observing the image to bring the end surface 12a of the shielding material onto the optical axis $O_L$ as shown in FIG. 7(b).

The positional adjustment of the shielding material 12 has been described so far. If the specimen stage pullout mechanism 3 is closed by this positional adjustment, the end surface 12a of shielding material 12 is placed on the center axis $O_i$ of the ion beam $I_B$.

When the positional adjustment of the shielding material 12 is made in this way, positional adjustment of the sample 6 is next made. That is, the position at which the sample 6 is processed is set under the condition where the sample stage pullout mechanism 3 has been opened as shown in FIG. 2. When this position is set in this manner, the optical microscope 15 is placed over the sample 6 as shown in FIG. 2. The shielding material 12 is also placed over the sample 6.

Figure 8:
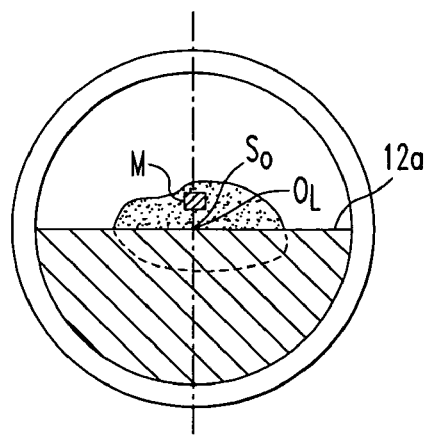
FIG. 8 illustrates the positional adjustment of a sample.

The operator first manipulates the sample X-translation knob (not shown) and the sample Y-translation knob (not shown) of the sample position-adjusting mechanism 5 to move the sample 6 in the X- and Y-directions. He observes the surface of the sample 6 with the optical microscope 15. After ion beam processing, if the operator finds a sample portion from which a cross section should be obtained, he manipulates the sample X-translation knob and the sample Y-translation knob to bring this sample portion into a position located just under the end surface 12a of the shielding material 12 as shown in FIG. 8. At this time, he also manipulates the sample rotation knob (not shown) of the adjusting mechanism 5 to rotate the sample such that the sample portion from which a cross section should be obtained is brought just under the end surface 12a.

The manner in which the sample 6 is placed in a position where it is processed has been described so far. When the sample stage pullout mechanism 3 is closed, the sample processing position $S_0$ (FIG. 8) placed in position on the optical axis $O_L$ of the optical microscope 15 as described above is placed on the center axis $O_i$ of the ion beam $I_B$. In FIG. 8, a substance M that is not easily etched by the ion beam is present in the sample 6.

After the positional adjustment of the optical microscope 15, the positional adjustment of the shielding material 12, and the positional setting of the sample 6 at the processing position are performed in this way, ion beam processing of the sample 6 set in the processing position as shown in FIG. 8 is next performed.

For the ion beam processing, the optical microscope 15 is retracted from the position located above the sample 6, and the sample stage pullout mechanism 3 is closed as shown in FIG. 5(b). The pullout mechanism 3 is closed under the condition where the shielding material 12 is placed over the sample 6, as shown in FIG. 8. Since the operator switches on the switch 9 of the electromagnet after placing the shielding material 12 over the sample 6 in this way, the shielding material 12 made of a magnetic material is firmly fixed to the yoke pieces 7b and 7c of the holder 7.

Figure 9A:
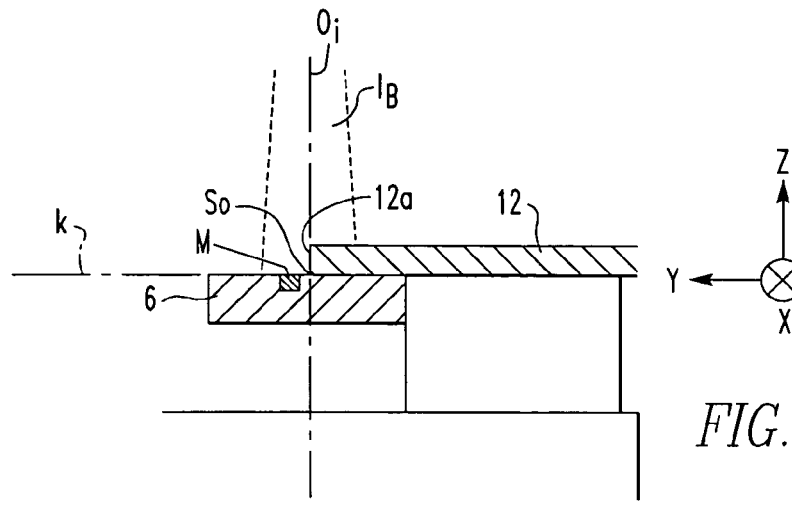
FIGS. 9(a), 9(b), and 9(c) illustrate ion beam processing of a sample.

When the sample stage pullout mechanism 3 is closed, the sample processing position $S_0$ is placed on the center axis $O_i$ of the ion beam $I_B$ as mentioned previously (FIG. 9(a)). The tilting axis k of the sample stage 4 is perpendicular to the center axis $O_i$ of the beam $I_B$ as also shown in FIG. 9(a). The end surface 12a is located on the center axis $O_i$ of the beam $I_B$ as shown also in FIG. 9(a).

Figure 9B:
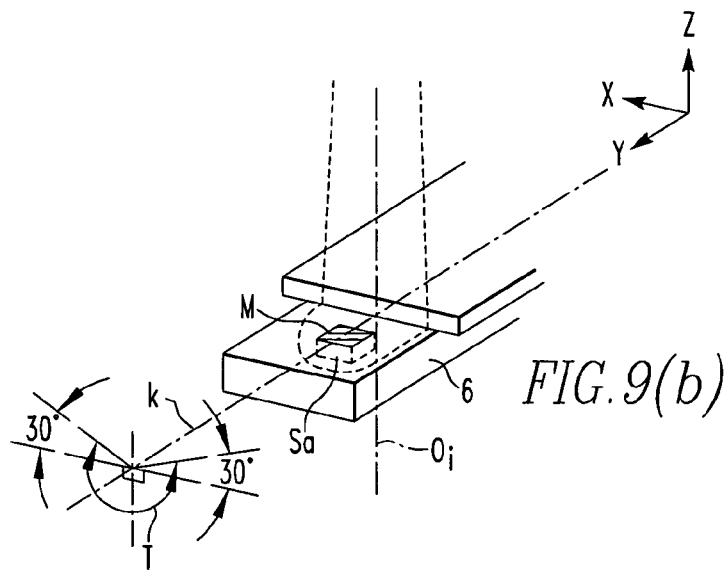

After the processing chamber 18 is evacuated by the pumping system 17, the ion beam $I_B$ is emitted from the ion gun 2. The portion of the beam $I_B$ not shielded by the shielding material 12 etches the surface of the sample 6 for a given time. Furthermore, in the sample preparation apparatus shown in FIG. 2, during ion etching of the sample 6, the tilting drive source 4a is operated to tilt the sample stage 4 reciprocably about the tilting axis k left and right. Therefore, as shown in FIG. 9(b), the sample 6 is ion-etched while reciprocably tilted together with the shielding material 12 as indicated by the arrow T. The portion Sa (FIG. 9(b)) is shielded by the substance M and cannot be etched as the prior art is etched. As a result, the substance M can be isolated from the sample 6. The tilt angle and tilting speed of the sample stage 4 provided by tilting drive 4a are appropriately determined. For example, as shown in FIG. 9(b), one tilting movement (i.e., one reciprocation) of ±30° is performed in 30 seconds. This movement is repeated (i.e., continuously reciprocating/rocking).

Figure 9C:
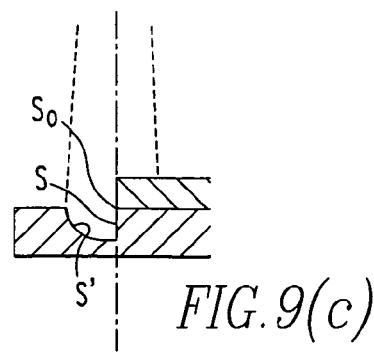

Finally, the portions on the sample 6 which are at the sample processing position $S_0$ and its surroundings are etched by the incident ion beam $I_B$ with the boundary defined by the end surface 12a of the shielding material 12 as shown in FIG. 9(c). In FIG. 9(c), indicated by S is a cross section of the sample that the operator wants to obtain. The cross section S will be observed later with a scanning electron microscope or other instrument.

Ion beam processing of the sample 6 performed by the sample preparation apparatus shown in FIG. 2 has been described so far. As mentioned previously, in the sample preparation apparatus of FIG. 2, the sample is ion-etched while the sample stage is tilted. Therefore, if the substance M that is not easily ion-etched as shown in FIGS. 8 and 9(a) to 9(c) is present in the sample, the substance M can be separated from the sample. Consequently, as shown in FIG. 9(c), unetched portions are prevented from being left behind before the desired cross section S of the sample is obtained, unlike in the prior art. As a result, the cross section S can be observed well with a scanning electron microscope or the like.

In the sample preparation apparatus of FIG. 2, the shielding material 12 is forcedly fixed to the yoke pieces 7b and 7c of the sample holder 7 by the electromagnet. Therefore, during ion etching of the sample 6, the relative position between the shielding material 12 and sample 6 does not deviate. For this reason, the selected surface of the sample is etched well for a long time by the ion beam.

While the sample preparation apparatus of FIG. 2 has been described so far, the present invention is not limited thereto.

Figure 10A:
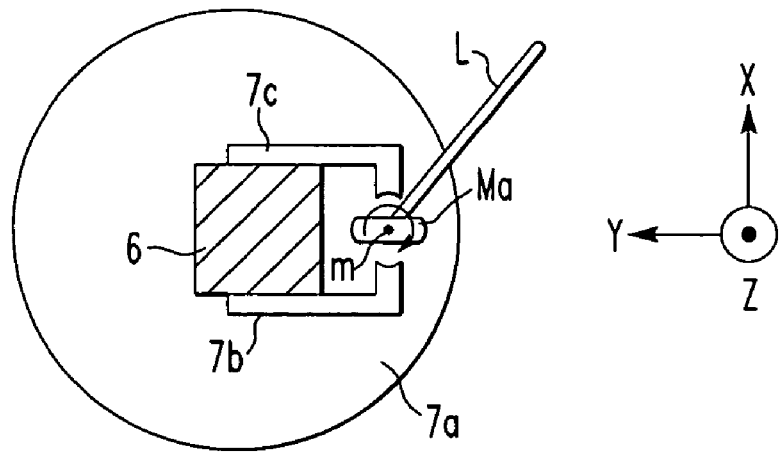
FIGS. 10(a) and 10(b) illustrate another embodiment of the present invention.
Figure 10B:
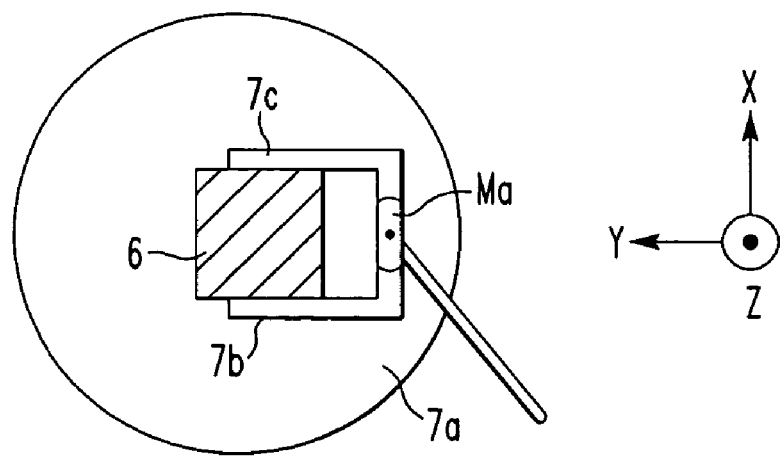

For example, in the above-described embodiment, an electromagnet is used as shown in FIGS. 3(a) to 3(c). Instead, a permanent magnet Ma may be used as shown in FIGS. 10(a) and 10(b) without using an electromagnet. FIGS. 10(a) and 10(b) correspond to FIG. 3(b). The magnet Ma is mounted to the holder-mounting portion 7a so as to be rotatable about an axis m parallel to the Z-axis. A lever L is mounted to the magnet Ma. The yoke pieces 7b and 7c, each made of a magnetic material, form an L-shaped yoke as shown in FIGS. 10(a) and 10(b).

In this structure, when the operator places the shielding material 12 on the yoke pieces 7b and 7c, he manipulates the lever L to fix the shielding material 12. The magnet Ma is brought into contact with the yoke pieces 7b and 7c as shown in FIG. 10(b). A strong magnetic field is produced between the yoke pieces 7b and 7c. The shielding material 12 is firmly fixed to the yoke pieces 7b and 7c acting as magnets.

Figure 11A:
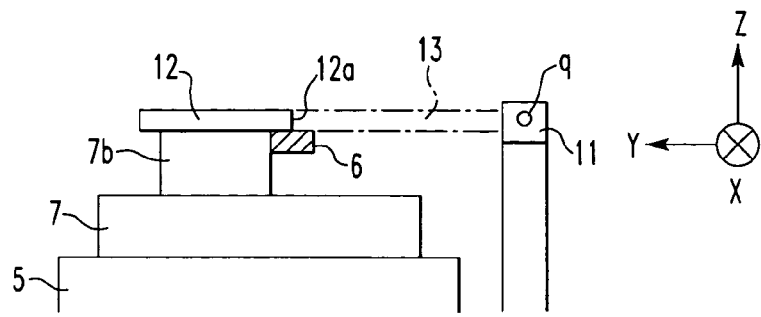
FIGS. 11(a), 11(b), and 11(c) illustrate a further embodiment of the present invention.
Figure 11B:
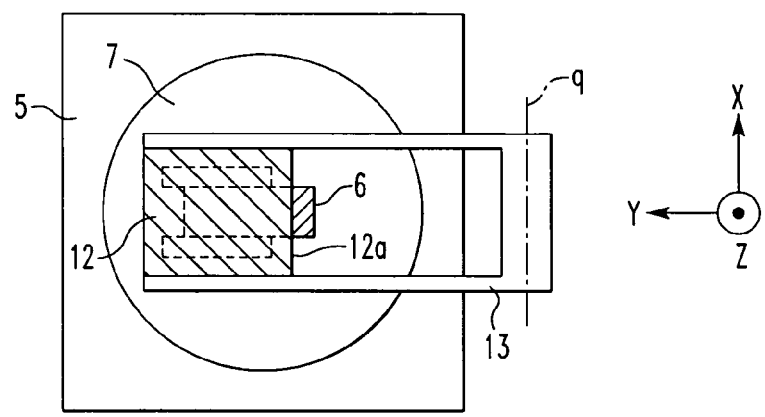
Figure 11C:
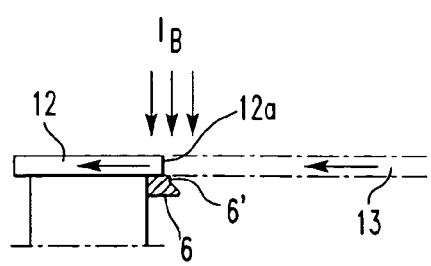

In the above-described embodiment, the processed portion of the sample is located to the left of the end surface 12a of the shielding material 12 as shown in FIGS. 4(a) and 4(b). Instead, the shielding material 12 may be held to the shielding material-holding mechanism 13 as shown in FIGS. 11(a), 11(b), and 11(c). The sample 6 may be held to the yoke pieces 7b and 7c. The processed portion of the sample may be placed to the right of the end surface 12a of the shielding material 12.

In this structure, during ion beam processing, the shielding material-holding mechanism 13 lengthens in its longitudinal direction (Y-direction) by thermal expansion as indicated by the arrow in FIG. 11(c). Therefore, even if the end surface 12a moves to the left (in the Y-direction), the processed surface 6' of the sample 6 is kept irradiated with the ion beam. Consequently, the previously etched, processed surface is kept clean at all times.

Furthermore, in the above-described embodiment, the shielding material 12 takes the form of a flat plate. Instead, a wire-like shielding material of circular cross section or belt-like shielding material of rectangular cross section may be used as described in the above-cited Japanese patent. A sample for TEM may be prepared using this shielding material.

In addition, in the above-described embodiment, ion beam processing is performed while the sample stage is tilted. Instead, ion beam processing may be performed while tilting the ion gun 2 without tilting the sample stage such that the stage is fixed. In this case, in FIG. 2, the ion gun 2 is mounted to the vacuum chamber 1 so as to be tiltable about the Y-axis. During tilting of the gun 2, the sample 6 is irradiated with the ion beam.

Further, plural ion guns may be arranged in the vacuum chamber. The sample stage may not be tilted but fixed. Under this condition, ion beams may be simultaneously directed at the sample from the guns. At this time, the guns may be arranged on a plane that is parallel to the XZ-plane of FIG. 2 and includes the center axis $O_i$ of the ion beam.

Figure 12:
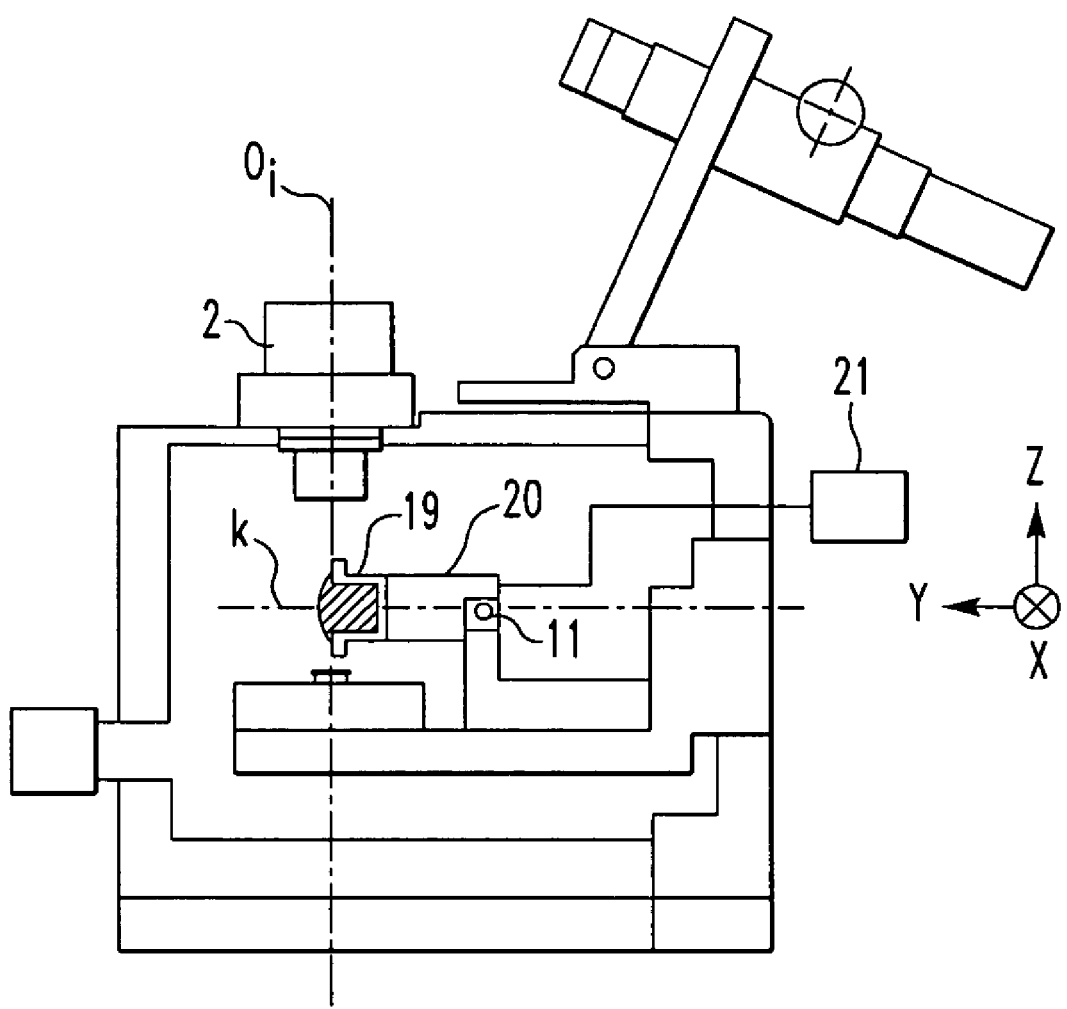
FIG. 12 illustrates still another embodiment of the present invention.

FIG. 12 shows an example in which a rotary sample holder 19 is mounted to the sample preparation apparatus shown in FIG. 2. For this purpose, a holder-rotating mechanism 20 is mounted to the shielding material-tilting mechanism 11 instead of the shielding material-holding mechanism 13. The rotary sample holder 19 is mounted to the front end of the rotating mechanism 20. A rotating drive source 21 is connected with the rotating mechanism 20, which creates motor rotation within it. Consequently, the sample holder 19 is rotated about the Y-axis.

Figure 13A:
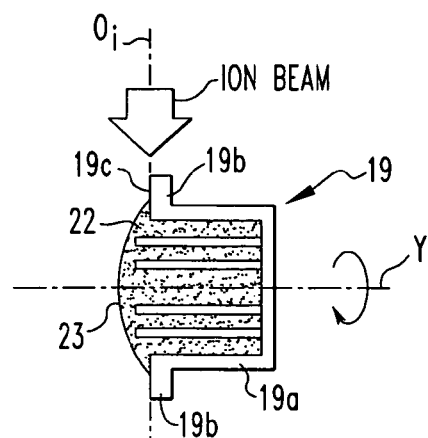
FIGS. 13(a), 13(b), and 13(c) illustrate yet another embodiment of the present invention.

FIG. 13(a) illustrates the rotary sample holder 19 of FIG. 12. The holder 19 has a cylindrical container portion 19a having a bottom and a jaw 19b formed in the entrance of the container portion 19a. The container portion 19a holds a sample 22 therein. The jaw 19b acts as the aforementioned shielding material. An end surface 19c of the shielding material 19b is located on the center axis $O_i$ of the ion beam. The end surface 19c is parallel to the XZ-plane perpendicular to the Y-axis. The jaw (shielding material) 19b is made of a substance that is not easily etched by the ion beam. Plural rod-like thin samples 22 are bonded to the sample holder with resin 23.

Figure 13B:
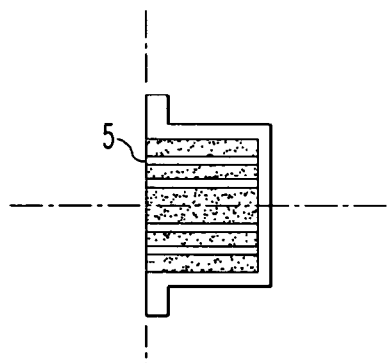

During ion beam processing, the ion beam is directed from the ion gun 2 at the samples while the rotary sample holder 19 is rotated at a given speed by the holder-rotating mechanism 20. Therefore, the sample and resin are etched as shown in FIG. 13(b) by the ion beam directed at them with the boundary defined by the end surface 19c of the sample holder 19. A cross section S of the sample produced by the ion etching will be observed later with a scanning electron microscope or other instrument. In this embodiment, the sample holder and shielding material are fabricated integrally. Therefore, any mechanism holding the shielding material is not necessary. In addition, it is not necessary to adjust the positional relation between the shielding material and sample.

Figure 13C:
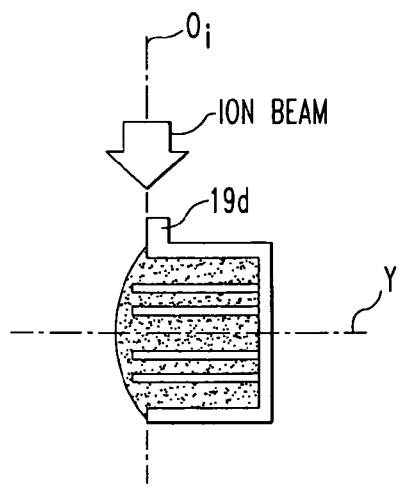

In the embodiment shown in FIG. 13(a), the jaw (shielding material) 19b is formed over the whole periphery of the entrance of the container portion. As shown in FIG. 13(c), a jaw 19d (shielding material) may be formed over a part of the entrance of the container portion. In this case, the sample may be tilted about the Y-axis during ion beam irradiation such that the ion beam hits the sample via the jaw 19d. Furthermore, the ion beam may be directed at the sample via the jaw 19d without tilting the sample (i.e., maintaining the sample fixed).

In the embodiment shown in FIGS. 13(a), 13(b), and 13(c), the rod-like sample is held to the sample holder with resin. A powdered sample may be held to the sample holder with resin. A cross section of the powdered sample produced by ion etching may be observed with a scanning electron microscope or other instrument.

Additionally, the sample preparation apparatus according to the present invention may be used for preparation of samples observed with an electron probe microanalyzer, Auger microprobe, or other similar instrument.

Having thus described our invention with the detail and particularity required by the Patent Laws, what is desired protected by Letters Patent is set forth in the following claims.

The invention claimed is:

1. A sample preparation apparatus comprising:
   ion beam irradiation means disposed in a vacuum chamber and directing an ion beam at a sample;
   a tilting sample stage disposed in the vacuum chamber and having a tilting axis substantially perpendicular to the ion beam;
   a sample stage tilting drive for continuously reciprocating the sample stage; and
   a sample holder disposed on the tilting sample stage, said sample holder comprising a container fabricated of a shielding material shielding a part of the ion beam directed at the sample held in said container,
   wherein the sample is processed by the ion beam while varying the tilt angle of said tilting sample stage,
   wherein said sample holder has an end surface substantially parallel to a plane that is perpendicular to said tilting axis, and wherein said sample is processed by the ion beam passed alongside the end surface.

2. A sample preparation apparatus as set forth in claim 1, wherein said sample holder has a container portion for accommodating the sample, the container having an entrance portion, and wherein a jaw forming said shielding material is formed in or over said entrance portion.

3. A sample preparation apparatus comprising:
ion beam irradiation means disposed in a vacuum chamber for directing an ion beam at a sample;
a sample stage disposed in the vacuum chamber;
a sample holder disposed on the sample stage and holding the sample, said sample holder comprising a container fabricated of shielding material for shielding a part of the ion beam directed at the sample held in said container, and
said ion beam irradiation means is tiltably mounted in the vacuum chamber and provided with a tilting drive such that the angle of incidence of the ion beam to a surface of the sample is continuously variable,
wherein the sample is processed by the ion beam while varying the tilt angle of said ion beam irradiation means,
wherein said sample holder has an end surface substantially parallel to a plane that is perpendicular to said tilting axis, and wherein said sample is processed by the ion beam passed alongside the end surface.

4. A sample preparation apparatus comprising:
ion beam irradiation means disposed in a vacuum chamber and directing an ion beam at a sample;
a tilting sample stage disposed in the vacuum chamber and having a tilting axis substantially perpendicular to the ion beam;
a sample stage tilting drive for reciprocating the sample stage;
a sample holder disposed on the tilting sample stage and holding the sample;
a shielding material in the form of a flat plate positioned over the tilting sample stage and shielding a part of the ion beam directed at the sample; and
a shielding material fixing means for fixing said shielding material to said sample holder, wherein said shielding material is in contact with said sample holder,
wherein the sample is processed by the ion beam while varying the tilt angle of said tilting sample stage.

* * * * *

UNITED STATES PATENT AND TRADEMARK OFFICE
CERTIFICATE OF CORRECTION

| | | |
|---|---|---|
| PATENT NO. | : 7,722,818 B2 | Page 1 of 1 |
| APPLICATION NO. | : 10/942752 | |
| DATED | : May 25, 2010 | |
| INVENTOR(S) | : Hasegawa et al. | |

It is certified that error appears in the above-identified patent and that said Letters Patent is hereby corrected as shown below:

Title page, insert the following:

Item -- (30) Foreign Application Priority Data
September 16, 2003 (JP) .......................2003-323248 --

Signed and Sealed this

Twenty-seventh Day of July, 2010

David J. Kappos
*Director of the United States Patent and Trademark Office*